(12) United States Patent
Ferchmin (10) Patent No.: US 9,717,746 B2
(45) Date of Patent: Aug. 1, 2017

(54) USE OF EDELFOSINE AND OTHER SYNTHETIC ETHER ALKYL-LYSOPHOSPHOLIPIDS (APLS) FOR SEIZURES AND RELATED DISEASES

(71) Applicant: Peter Andrew Ferchmin, San Juan, PR (US)

(72) Inventor: Peter Andrew Ferchmin, San Juan, PR (US)

( * ) Notice: Subject to any disclaimer, the term of this patent is extended or adjusted under 35 U.S.C. 154(b) by 0 days.

(21) Appl. No.: 14/571,511

(22) Filed: Dec. 16, 2014

(65) Prior Publication Data

US 2016/0166588 A1  Jun. 16, 2016

(51) Int. Cl.
| | | |
|---|---|---|
| *A61K 31/075* | (2006.01) | |
| *A61K 31/08* | (2006.01) | |
| *A61K 31/14* | (2006.01) | |
| *A61K 31/66* | (2006.01) | |
| *A61K 31/661* | (2006.01) | |
| *A61K 31/675* | (2006.01) | |

(52) U.S. Cl.
CPC .......... *A61K 31/661* (2013.01); *A61K 31/075* (2013.01); *A61K 31/08* (2013.01); *A61K 31/14* (2013.01); *A61K 31/66* (2013.01); *A61K 31/675* (2013.01)

(58) Field of Classification Search
CPC ...... A61K 31/075; A61K 31/08; A61K 31/14; A61K 31/66
See application file for complete search history.

(56) References Cited

U.S. PATENT DOCUMENTS

| | | | | |
|---|---|---|---|---|
| 2007/0027184 A1* | 2/2007 | Malecha | ............... | C07D 401/12 514/311 |
| 2016/0060260 A1* | 3/2016 | Palmer | ................ | C07D 471/04 514/234.5 |

* cited by examiner

*Primary Examiner* — Yong Chong
(74) *Attorney, Agent, or Firm* — Harbin & Hein PLLC (57) ABSTRACT

Synthetic ether alkyl-lysophospholipids (APLs) provide an effective treatment for subjects suffering from cholinergic seizures. Among other uses, APLs may be used to treat the effects of epileptic seizures in particular cholinergic seizures caused by exposure to insecticides or chemical warfare nerve agent exposure. Edelfosine, an APL, has been show to be particularly effective in these areas.

2 Claims, 10 Drawing Sheets

USE OF EDELFOSINE AND OTHER SYNTHETIC ETHER ALKYL-LYSOPHOSPHOLIPIDS (APLS) FOR SEIZURES AND RELATED DISEASES

BACKGROUND OF THE INVENTION

Edelfosine is a well-known compound that has been researched and studied predominately for anti-cancer treatments for many years. Edelfosine has not, however, been the subject of study to see its effects on seizures and other neurological disorders and diseases. What we have found through research and study is that edelfosine surprisingly has good results in alleviating seizures, in particular cholinergic seizures, which result from overstimulation of muscarinic receptors.

Cholinergic muscarinic overstimulation can be achieved by irreversible inhibitors of acetylcholinesterase, like chemical warfare nerve agents (CWNA) (de Araujo Furtado, M. et al., 2012), or muscarinic agonists. Pilocarpine, a muscarinic agonist, overstimulates M1 muscarinic receptors causing acute seizures followed days later by chronic seizures that emulate clinical epilepsy. It is possible that status epilepticus (SE) naturally increases brain acetylcholine and choline (Carriere, J. L. El-Fakahany, E. E., 2000, Costa, L. G. Murphy, S. D., 1984), which overstimulates M1 receptors (Jope, R. S. Gu, X., 1991). In all cases, muscarinic hyperstimulation enhances the release of glutamate, causes seizures, excitotoxicity, astrocytes activation, neuronal death and brain injury. Interestingly the link between muscarinic hyper-stimulation and the resulting glutamate excitotoxicity was heretofore unknown. This gap of knowledge is an impediment for the development of novel therapeutic interventions targeting early steps of CWNA toxicity and yet unexplored processes leading to SE.

Based on our research and study of these mechanisms, we have found surprisingly that edelfosine can effectively prevent the effects of seizures, which may be particularly useful for subjects suffering from epilepsy or chemical nerve agent exposure. It also appears that edelfosine may be helpful for seizures relating to Alzheimer's disease, as about 20% of Alzheimer's patients develop unprovoked late onset seizures. Further, other synthetic ether alkyl-lysophospholipids (APLs) show promise in similarly reducing seizures. Such molecules include perifosine.

SUMMARY OF THE INVENTION

Therefore, it is an object of the present invention to treat subjects suffering from seizures by administering to that subject an effective amount of edelfosine or a pharmaceutically acceptable salt thereof. It is a further object of the invention to treat subjects suffering from seizures by administering to that subject an effective amount of a different APL or a pharmaceutically acceptable salt thereof. Nonlimiting uses include treating seizures caused by epilepsy or exposure to warfare chemical nerve agents or other chemicals that indirectly stimulate the muscarinic receptors.

BACKGROUND

Figure 10:
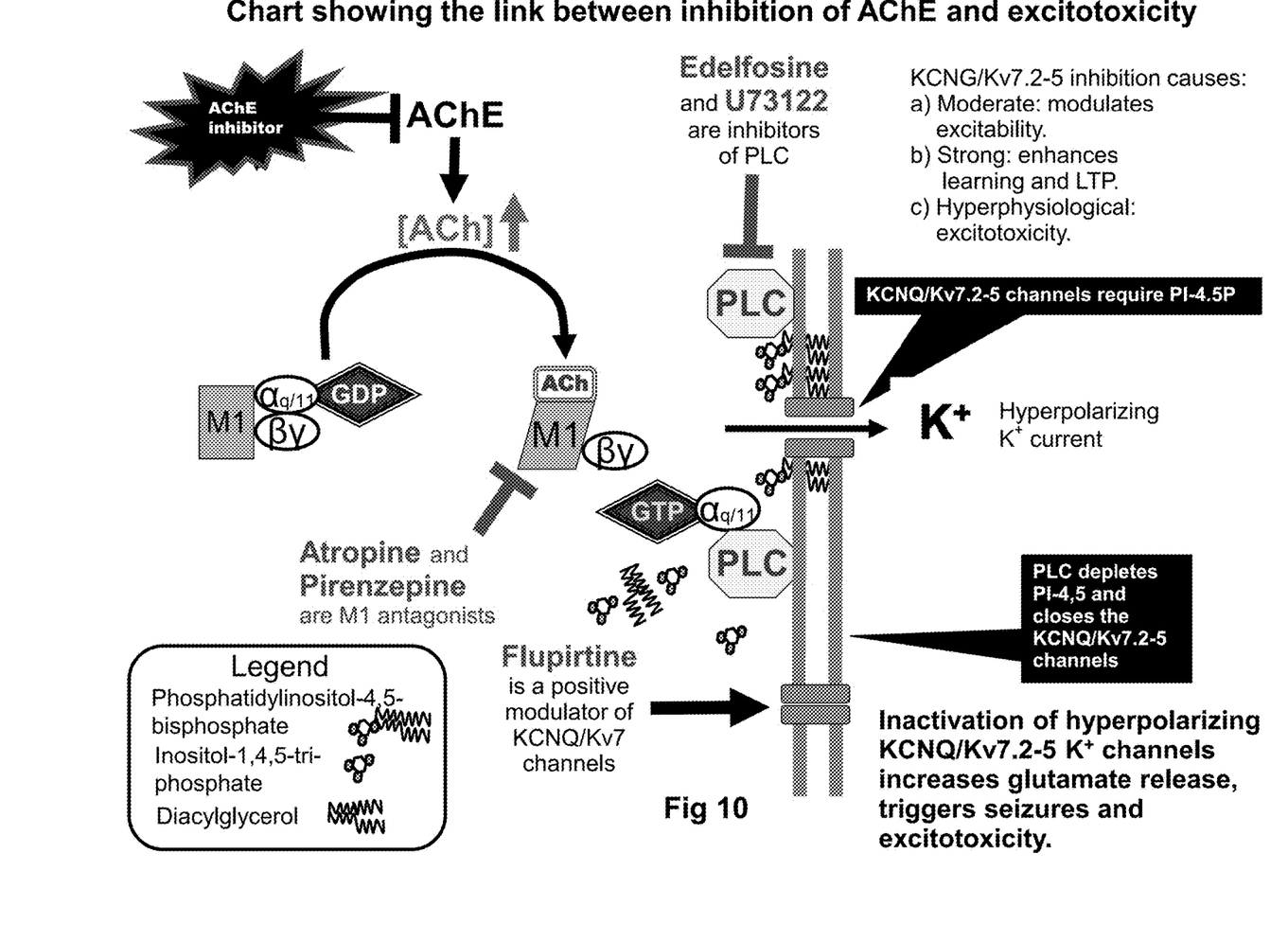
FIG. 10. Illustration showing the link between inhibition of AChE and excitotoxicity and the proposed mechanism of action for edelfosine.

We have learned that the activation of M1 muscarinic receptors coupled to protein $G_{q/11}$ activates the phospholipase C (PLC3β). This lipase depletes the pool of membrane phosphatidylinositol 4,5-bisphosphate required for the activity of the Kv7.2-7.5 (Kv7.x or KCNQ) potassium voltage gated channels, which mediate the hyperpolarizing M-current (Delmas, P. Brown, D. A., 2005). FIG. 10 further illustrates this. The inactivation of M-current lowers the threshold of neuronal excitability, enhances the release of glutamate, and causes seizures and excitotoxicity. This pathway is supported by the fact that two activators of Kv7.2-7.5 channels, retigabine and flupirtine, are being tested or marketed (in Europe, India and other countries) as antiepileptic, analgesic, or for other similar applications.

Methods of Slice Preparation and Electrophysiological Recordings.

We have conducted in vitro experiments. We used male Sprague-Dawley rats (120-200 g) from our colony for preparing acute hippocampal slices. We used a standard artificial cerebrospinal fluid (ACSF), containing (in mM) 125 NaCl, 3.3 KCl, 1.25 $NaH_2PO_4$, 2 $MgSO_4$, 2 $CaCl_2$, 25 $NaHCO_3$, and 10 glucose, for dissection and incubation. We performed the dissections at ice temperature; transverse slices were cut 400 µm in thickness with a manual slicer and immediately transferred to the recording chamber. Recording of extracellular field potentials or population spikes (PSs) was done as described (Ferchmin, P. A. et al., 2000).

Figure 1:
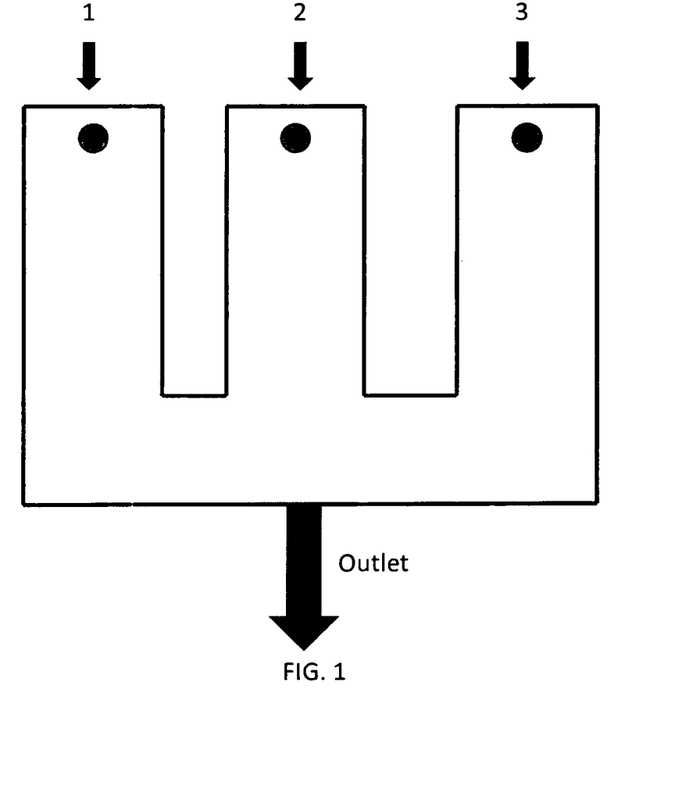
FIG. 1. Photograph of chamber containing hippocampal slices used for experiments.

Briefly, the chamber contains three lanes with independent perfusion lines exposed to the same gaseous phase (FIG. 1). The lower part of the chamber was filled with $H_2O$ kept at 37.4±1° C. and continuously bubbled with 95% $O_2$, 5% $CO_2$. We kept the slices at the gas-liquid interface, on an acrylic plate covered with nylon mesh (Hanes) located above the $H_2O$ perfused with ACSF and kept at 34±1° C. Before entering the chamber, the ACSF was continuously bubbled with 95% $O_2$, 5% $CO_2$ and warmed by flowing through a stainless steel capillary immersed in the lower part of the chamber. We kept the chamber's exterior at 30±1° C. Strict control of the temperatures at the three levels (outside, nylon mesh, and water bath) was indispensable to avoid variability of results in this system.

One hour after dissection, we recovered and stabilized the electrophysiological activity of the slices. At that time, we determined the PSs in each slice. We used a concentric bipolar electrode placed in stratum radiatum of the CA1 area to stimulate the slices with a constant current for 0.2 ms. The population spikes (PSs) were recorded in stratum pyramidale with a glass micropipette filled with 2 M NaCl and impedance ranging from 1 to 5 MΩ. FIG. 1 shows the incubation chamber without the lid exposing the three lanes with hippocampal slices.

Procedure for Testing Neurotoxicity

We based the procedure on that described in (Schurr, A. et al., 1995a, Schurr, A. et al., 1995b) as modified by us (Ferchmin, P. A., Perez, D. Biello, M., 2000) We distributed 10 to 30 slices among the three lanes; since slices from two animals were used, they were equally distributed among the lanes. Testing of slices started 1 h after dissection. A stimulus strength twice that required for eliciting a threshold population spike (PS) stimulated each slice. We recorded this initial PS and compared it with the response elicited by the same stimulus, recorded from the same position, after the completion of the corresponding experimental treatment. We used the percentage difference between the final and the initial PS remaining as a measure of recovery.

For FIGS. 2 to 9, the bar in the graphs show the percentage area of the PS recovered. Except for FIG. 7, the white bars correspond to the neurotoxicants alone and represent the damage without antidotes applied. Black bars represent the PS recovered after application of the neurotoxic stimulus followed by the antidote applied 15-30 min later. Grey dotted bars correspond to the PS recovered after 1 hour application of an antidote without any neurotoxicants.

Data Analysis

The areas of the PS (millivolts per millisecond) were acquired and analyzed with the Labman program (gift from Dr. T. J. Teyler WWAMI Medical Education Program, University of Idaho, Moscow, Id.). We statistically analyzed the data using SigmaPlot version 12.5 (SYSTAT Software). Analysis of variance was used whenever the data were distributed normally; otherwise, we used Kruskal-Wallis one-way analysis of variance on ranks followed in each case by the appropriate post hoc test. When two groups were compared, the t test was used.

Results

The In Vitro DFP Model. Edelfosine Reverses the Effect of DFP.

The experiments' goal was to study possible antidotes for the damage muscarinic hyper-stimulation inflicted. We applied all antidotes or experimental drugs after either DFP or the pilocarpine-high-potassium treatment.

Figure 2:
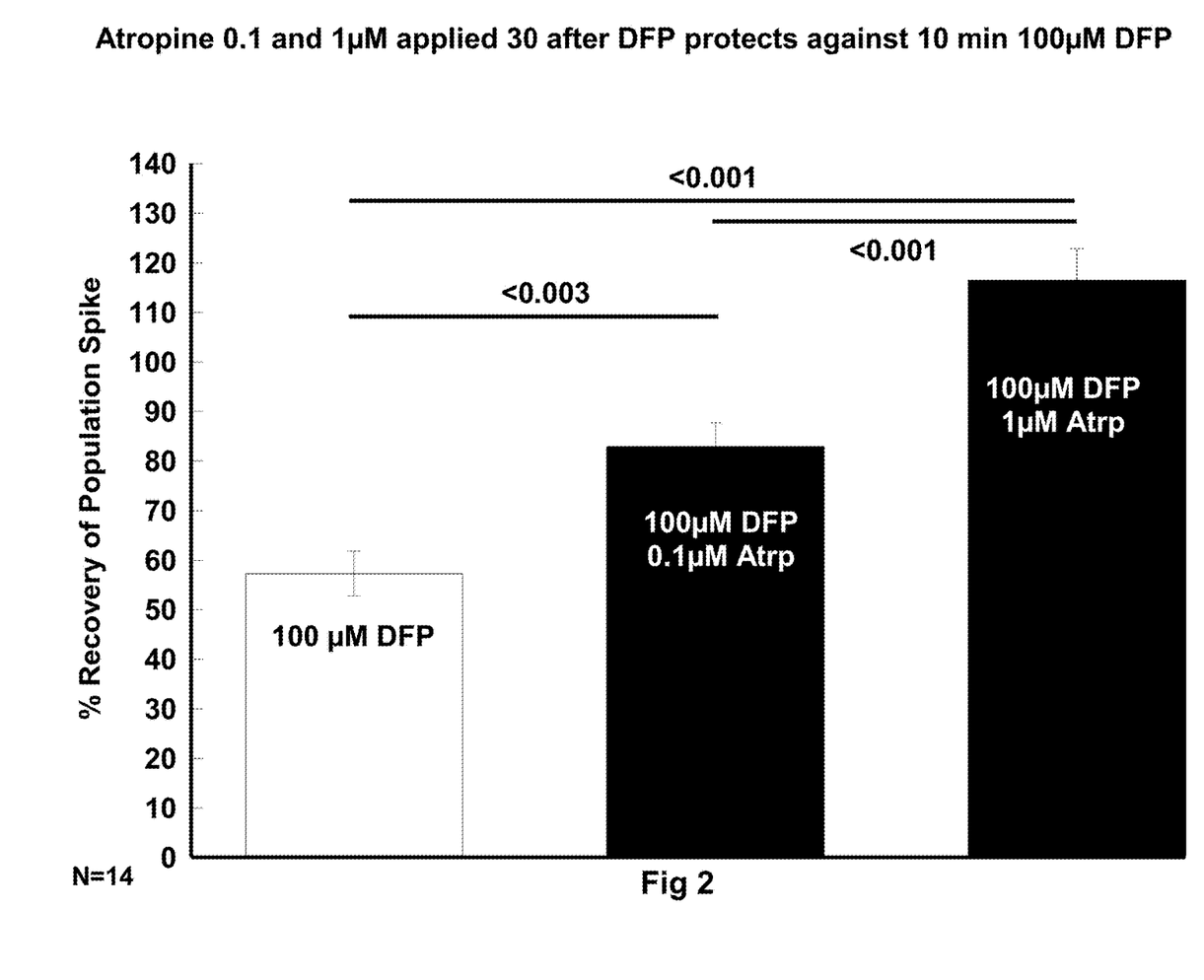
FIG. 2. Graph showing Atropine 0.1 and 1 µM applied 30 minutes after DFP protects against 10 min. 100 µM DFP.
Figure 3:
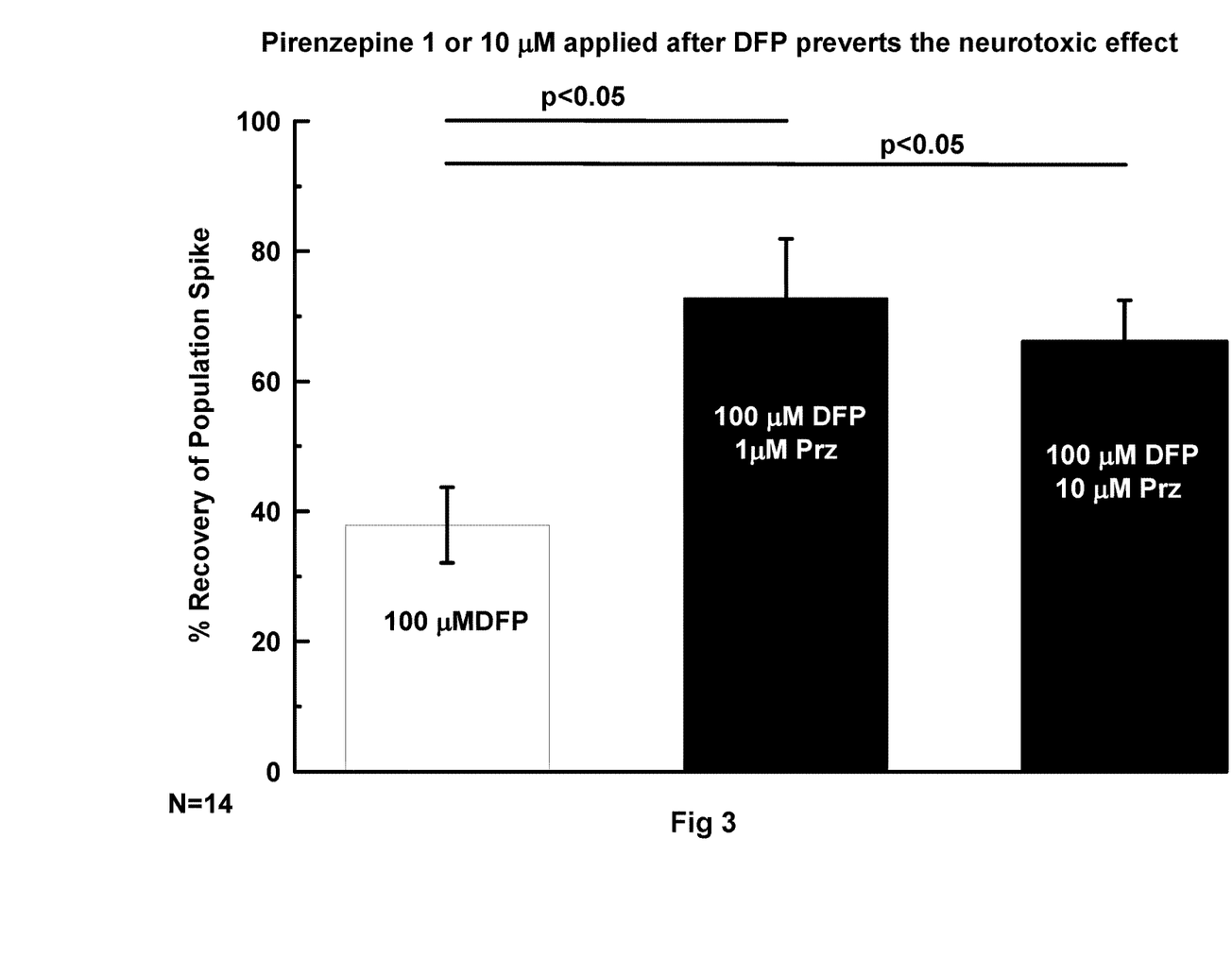
FIG. 3. Graph showing Pirenzepine 1 or 10 µM applied after DFP prevents a neurotoxic effect.
Figure 4:
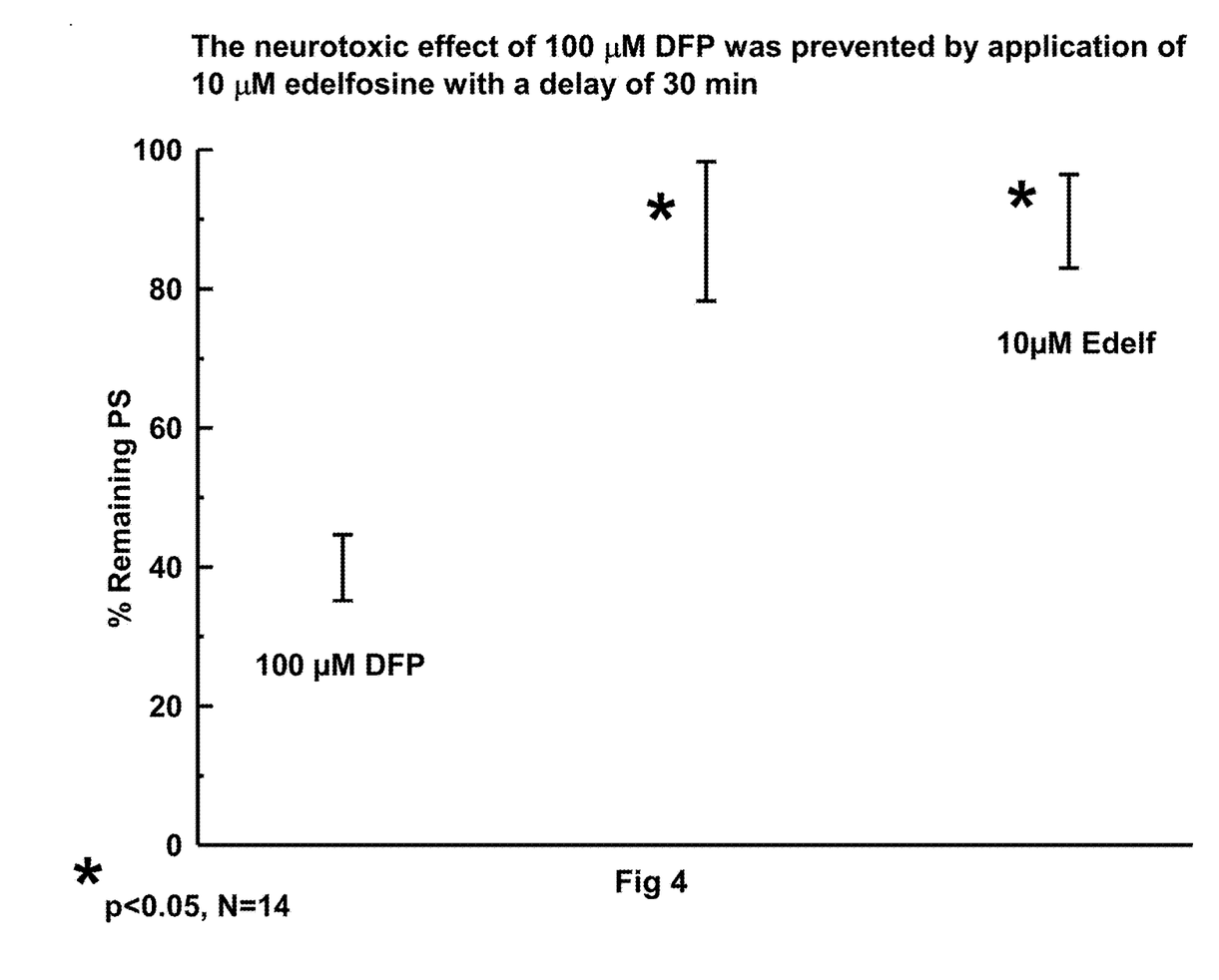
FIG. 4. Graph showing 10 µM edelfosine applied 30 minutes after 100 µM DFP prevents the neurotoxic effect of DFP.
Figure 5:
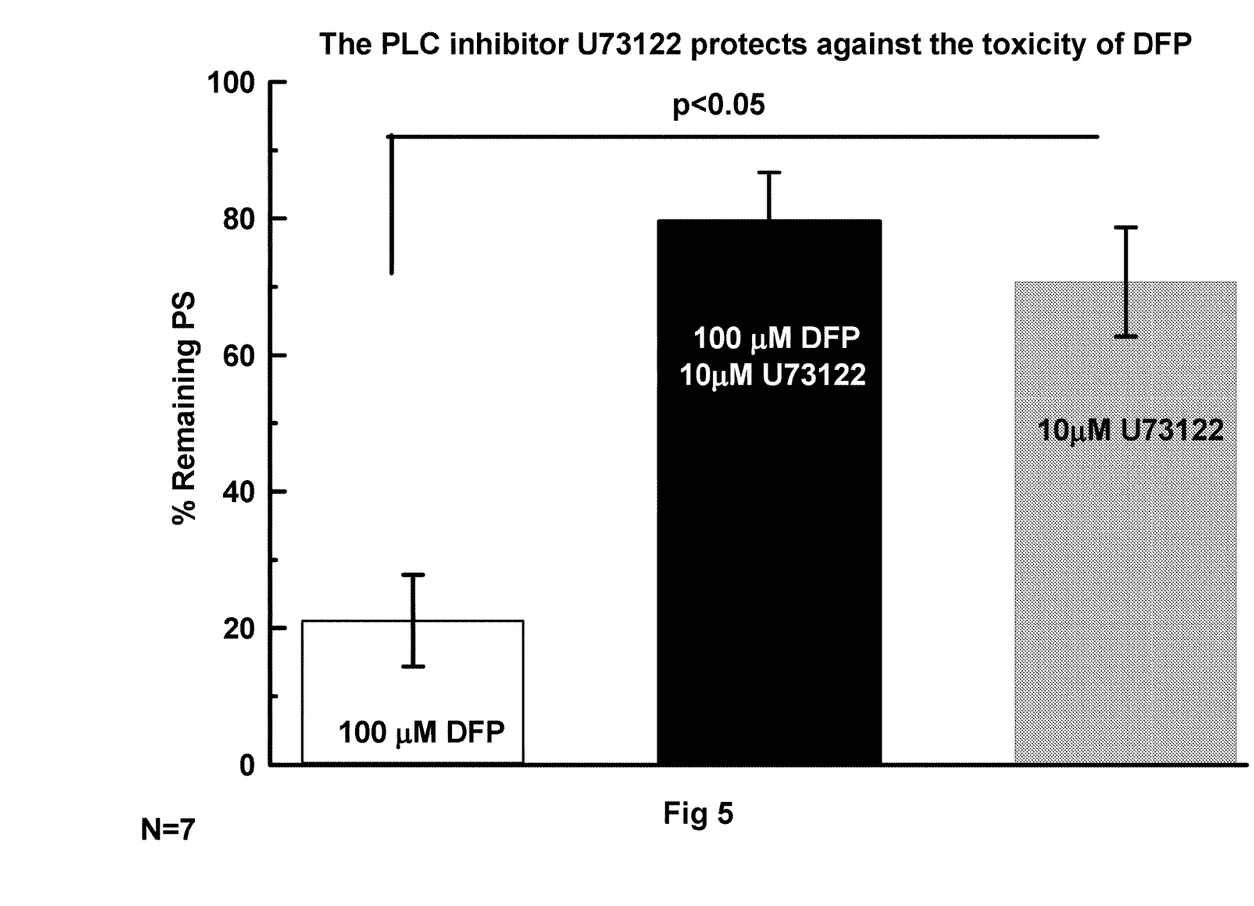
FIG. 5. Graph showing U73122 protection against DFP toxicity.
Figure 6:
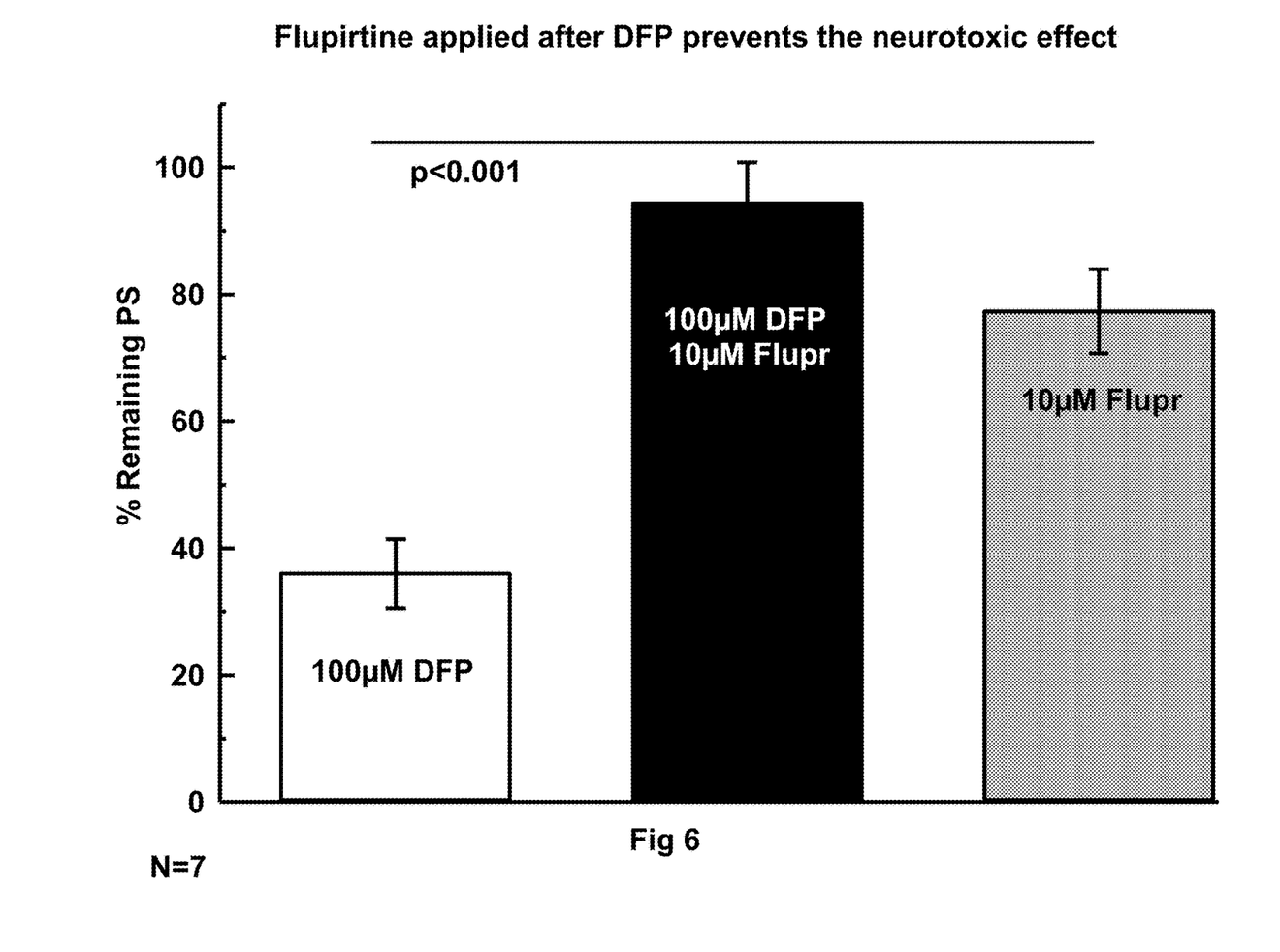
FIG. 6. Graph showing flupirtine preventing neurotoxic effect of DFP.

The muscarinic nature of the neurotoxic effect of DFP is confirmed in FIG. 2. Applying atropine after exposure of slices to DFP precludes the neurotoxic effect of this surrogate of the CWNA sarin. In FIG. 3, pirenzepine, a more selective antagonist for M1 muscarinic receptor, was applied after DFP. FIG. 4 clearly shown that 10 µM edelfosine applied 30 min after DFP protects and edelfosine per se is innocuous. Another PLC inhibitor, U73122, precludes the damage of DFP as edelfosine did (FIG. 5). The advantage of edelfosine is that is more selective than U73122. Flupirtine is an activator of M channels and acts downstream from the target of edelfosine. Flupirtine also prevents the toxic effect of DFP (FIG. 6).

The In Vitro Pilocarpine Model. Edelfosine Reverses the Effect of the Pilocarpine Treatment.

Figure 7:
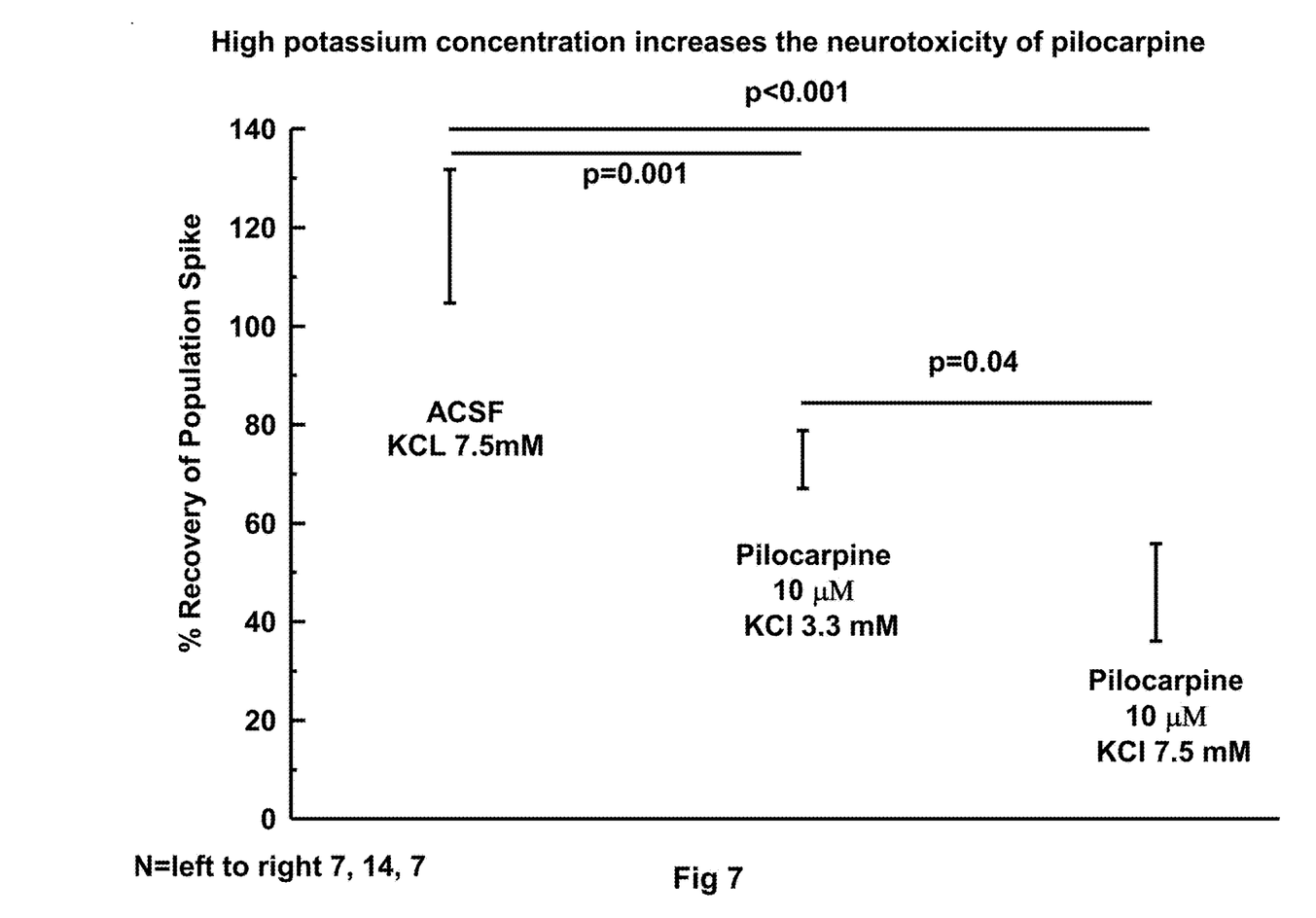
FIG. 7. Graph showing that high potassium concentration increases the excitability and thus recruits more neurons as shown in the first bar. The comparison of the second and third bars show that the neurotoxicity of pilocarpine increases at high potassium concentration.
Figure 8:
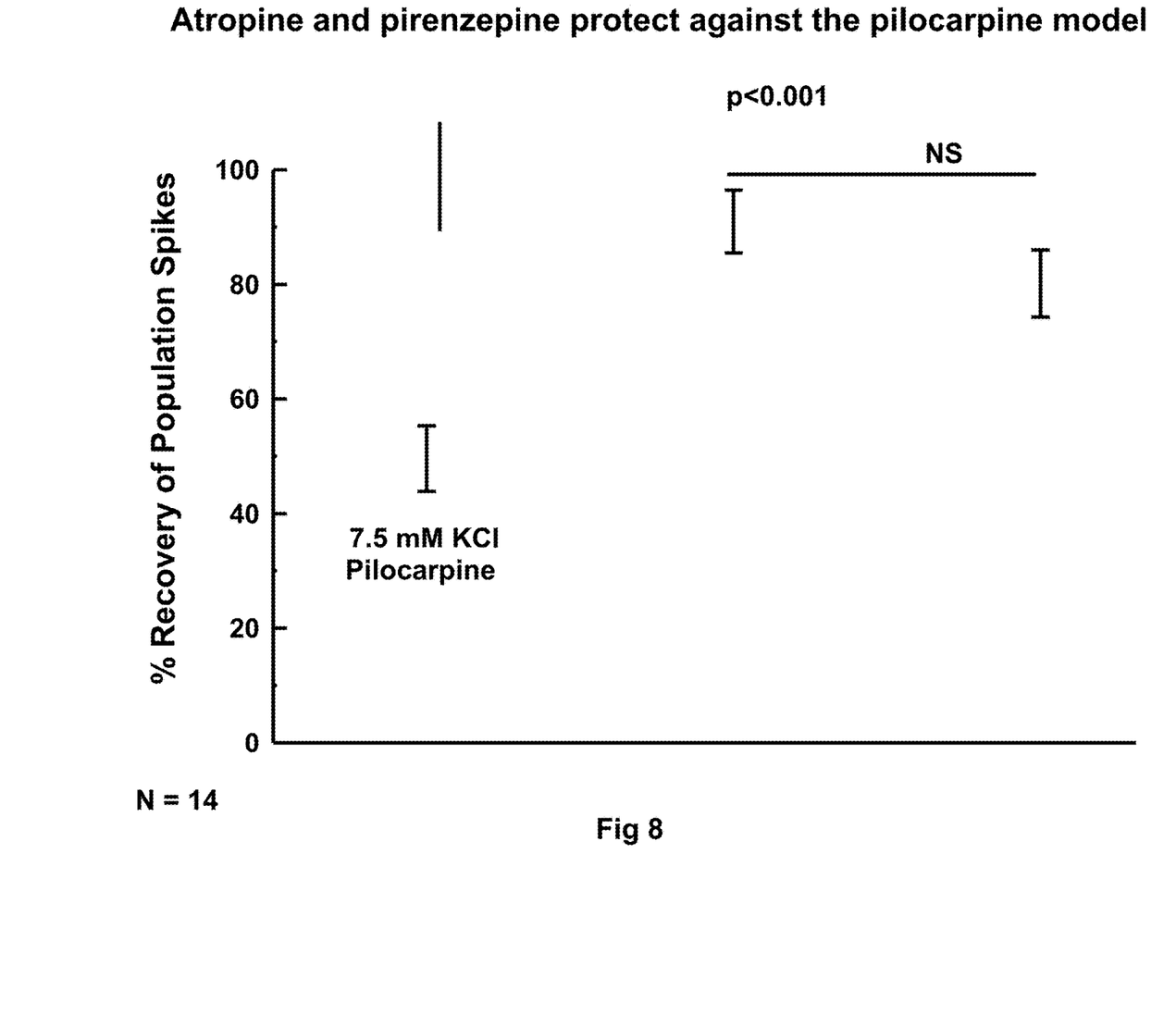
FIG. 8. Graph showing atropine and pirenzepine protecting against pilocarpine in the ex vivo pilocarpine epilepsy model.
Figure 9:
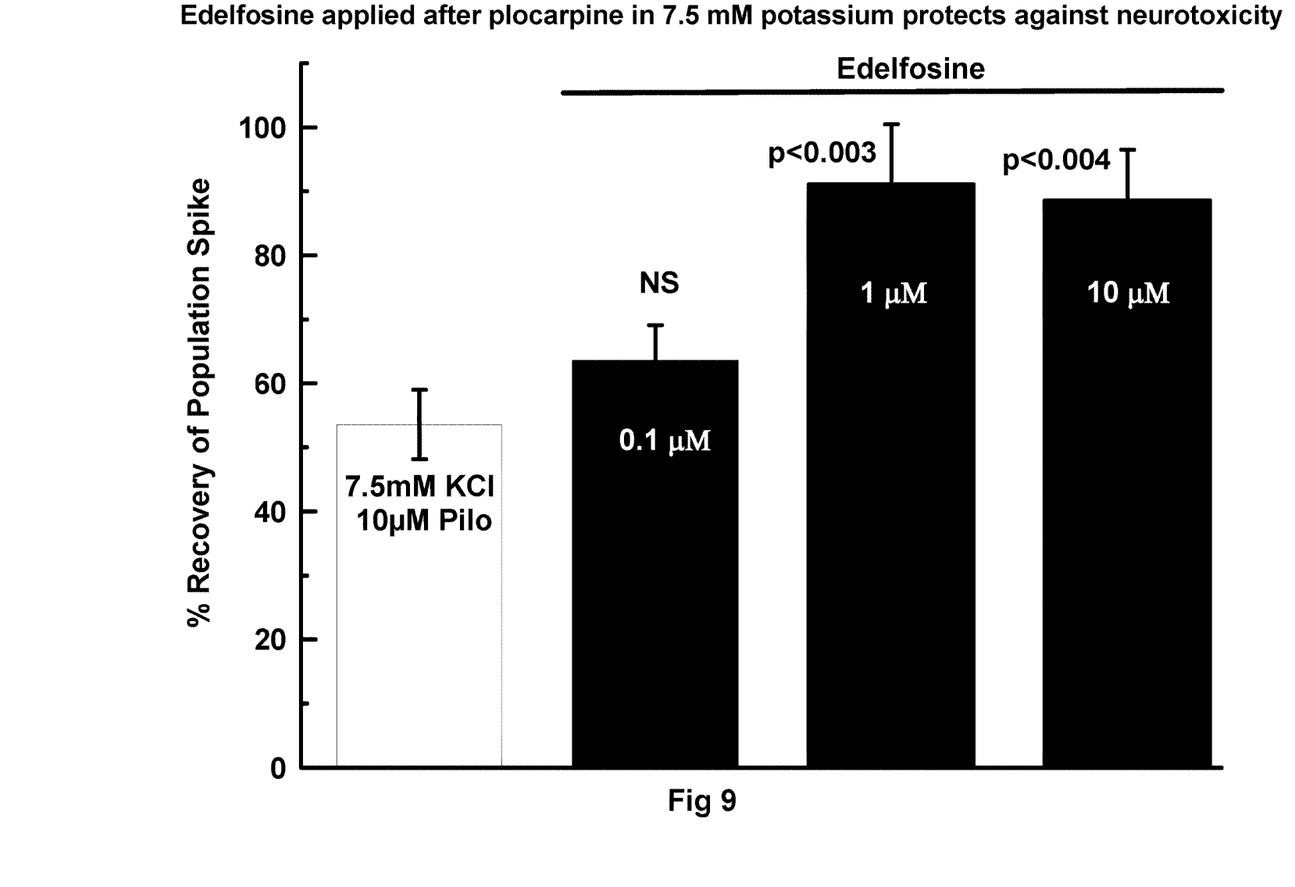
FIG. 9. Graph showing that 1 and 10 µM edelfosine applied after pilocarpine in 7.5 mM potassium protects against neurotoxicity.

The in vivo pilocarpine model of epilepsy (Scorza, F. A. et al., 2009, Turski, L. et al., 1989, Voutsinos-Porche, B. et al., 2004) was used for decades. We developed an ex vivo pilocarpine high potassium model in our lab based on (Rutecki, P. A. Yang, Y., 1998). FIG. 7 shows that this epilepsy model lowers the areas of PS. The role of M1 muscarinic receptor is evidenced by the efficacy of atropine and pirenzepine to avoid the loss of PS area (See FIG. 8). The effectiveness of 1 µM edelfosine is demonstrated in FIG. 9.

FIG. 10 puts in context all the data and confirms the proposed mechanism of action of edelfosine. Acetylcholinesterase (AChE) inhibitors prevent the breakdown of acetylcholine (ACh) and cause a toxic built up of this neurotransmitter. The increase concentration of ACh increases its binding to the cholinergic receptors, which become overstimulated. The most pertinent cholinergic receptor in the present case is the M1 muscarinic subtype. The M1 receptor is a membrane-embedded protein coupled to a G protein composed of three subunits $alpha_{q/11}$, beta, and gamma. After ACh binds the M1 receptor, the alpha subunit releases GDP, binds GTP, and dissociates from the beta and gamma subunits. The GTP-$alpha_{q/11}$ complex binds and activates the phospholipase C (PLC) which hydrolyzes the membrane lipid phosphatidylinositol-4,5-bis phosphate. This phospholipid is required for the activity of the Kv7.2-7.5 channels. The Kv7.2-7.5 (also known as KCNQ2-5) voltage gated potassium channel mediates the hyperpolarizing M-current Inhibition of the activity of these channels leads to uncontrolled neuronal depolarization that results in glutamate release, seizures, and excitotoxicity. The inhibition of PLC by edelfosine, U73122, or presumably other selective inhibitor of this enzyme will abrogate the effect of M1 activation by excessive ACh concentration. The concept that inhibition of PLC is a possible therapeutic procedure against M1 overstimulation in case of poisoning with irreversible AChE inhibitors or epileptic seizures is novel.

There are other antidotes against M1 stimulation. The most obvious is the routine clinical use of atropine, a nonselective muscarinic antagonist. Pirenzepine, a selective M1 inhibitor that does not cross the blood brain barrier was used here for experimental purposes. Activators of Kv7.2-7.5 channels, like flupirtine, also ameliorate the effect of M1 overstimulation.

Other Inhibitors of Phospholipase C as Putative Therapeutic Agents

The ether lipid 1-O-octadecyl-2-O-methyl-rac-glycero-3-phosphocholine, or ET-18-OCH(3), commonly known as edelfosine is the prototype molecule of a heterogeneous group of synthetic ether alkyl-lysophospholipids (APLs) sometimes referred to as antitumor ether lipids. Examples of other clinically promising APLs include octadecyl-(1,1-dimethyl-piperidinio-4-yl)-phosphate usually named perifosine and less frequently D-21266 or KRX-0401. Perifosine is being developed for possible cancer indications. Perifosine is structurally related to miltefosine. APLs inhibit phospholipase C beta, therefore, all APLs potentially could exert the same therapeutic effect as edelfosine. On the other hand 1-[6-[[(17β)-3-Methoxyestra-1,3,5(10)-trien-17-yl]amino]hexyl]-1H-pyrrole-2,5-dione (U73122) which is not an APL also inhibits PLC. Although U73122 causes untoward side effects, one or more of its analogues could be a useful therapeutic tool.

The invention claimed is:

1. A method for treating a subject suffering from seizures comprising administrating, to a person in need thereof, an effective amount of synthetic ether alkyl-lysophospholipid or a pharmaceutically acceptable salt thereof wherein said synthetic ether alkyl-lysophospholipid is edelfosine or perifosine.

2. The method of claim 1, wherein said seizures are caused from one or more of the group consisting of: Epilepsy or chemical nerve agents.

* * * * *